United States Patent [19]

Tunac

[11] Patent Number: 4,665,035
[45] Date of Patent: May 12, 1987

[54] FERMENTATION APPARATUS AND SYSTEMS FOR THE CULTIVATION OF MICROORGANISMS AND OTHER BIOLOGICAL ENTITIES

[76] Inventor: Josephino Tunac, 5284 Collington Dr., Troy, Mich. 48098

[21] Appl. No.: 866,764

[22] Filed: May 27, 1986

[51] Int. Cl.⁴ .............................................. C12M 1/24
[52] U.S. Cl. .................................... 435/296; 206/219; 215/DIG. 8; 422/102; 435/313; 435/316
[58] Field of Search ............... 435/296, 299, 313, 316; 206/219; 215/1 C, DIG. 1, DIG. 8; 422/102

[56] References Cited

U.S. PATENT DOCUMENTS

| | | | |
|---|---|---|---|
| 3,275,180 | 9/1966 | Optner et al. | 220/17 |
| 3,920,226 | 11/1975 | Walt | 259/72 |
| 4,027,427 | 6/1977 | Stoller et al. | 47/1.1 |
| 4,073,693 | 2/1978 | Janin | 435/296 X |
| 4,197,287 | 4/1980 | Piasio et al. | 424/1 |
| 4,303,616 | 12/1981 | Kano et al. | 422/102 |
| 4,477,208 | 10/1984 | Scott | 405/261 |

FOREIGN PATENT DOCUMENTS 137292  4/1985  European Pat. Off. ............ 422/102

*Primary Examiner*—Samuel Scott
*Assistant Examiner*—Allen J. Flanigan
*Attorney, Agent, or Firm*—Krass & Young

[57] ABSTRACT

Shake flask aerobic fermentation apparatus and systems having improved baffling and closuring are provided for improved microbial growths and increased oxygen absorption rates (OAR) approaching the levels obtainable in large-scale air-sparged fermentation vessels.

21 Claims, 21 Drawing Figures

FERMENTATION APPARATUS AND SYSTEMS FOR THE CULTIVATION OF MICROORGANISMS AND OTHER BIOLOGICAL ENTITIES

TECHNICAL FIELD

This invention relates to biotechnology and to improvements in flask or container apparatus and systems for aerobic fermentation, particularly fermentation vessel systems used for the cultivation in a liquid growth medium of a microorganism, cell line or other biological entity for improved production of cells or or products created by the growth of the biological entity.

The vessel systems of the invention using apparatus that is small in scale affords high aeration capacities approaching the levels obtainable in large air-sparged fermentation vessels so that the system can be used for developing or optimizing culture processes at low cost and scaling them up to large scale production.

BACKGROUND OF THE INVENTION

The rates of growth and the formation of products or metabolites by aerobic microorganisms are often regulated by the availability of dissolved oxygen in the culture medium. While a low level of dissolved oxygen inhibits the growth or production of certain microbial metabolites, concentration of oxygen above the critical level may not affect activity. For this reason, it is desirable to maintain high oxygen supply during the cultivation of aerobic organisms.

In stirred fermentors, aeration is carried out by injection or sparging of air into the vessel. In this process, a high level of dissolved oxygen is easily achieved. For media contained in flasks or tubes, aeration is essentially by simple gas-liquid contact: oxygen is transferred into the liquid culture from the gas head space. Thus, the surface area of the liquid medium is critical in the transfer process. The larger the surface area exposed, the better is the aeration for the medium. Exposure of the larger surface area is carried out by shaking the flask; this creates a vortex, exposing more liquid surface area to the head space.

Other methods devised to increase aeration include indentation of the flask or provision of baffles at the bottom of the flask. Thus, when the flask is shaken, the baffles break up the vortex and the liquid media is splashed, creating a considerable increase in surface area beyond that afforded by the vortex.

An increase in surface area of the medium inside the flask does not necessarily translate, however, to high aeration. The supply of air inside the vessel is another limiting factor. The length of the neck of the flask and the type of closure can greatly affect the flow of air to the surface of the liquid. Flasks or tubes used in the culturing of microorganisms are traditionally sealed with cotton plugs to prevent contamination. Cotton plugs, however, are not good closures in regard to air permeability; they offer considerable resistance to gas transfer. Consequently, cotton plugs allow only a low level of oxygen diffusing into the vessel and poor escape of carbon dioxide resulting in its build up inside the vessel.

Several improvements in closures have been introduced since the cotton plug, including loose-fitting stainless steel and plastic closures, gauze, foam pads, and silicone sponge plugs. The loose-fitting closures allow air to slip or diffuse from under the cap over the lip of the flask or tube, while cotton or gauze closures allow air to enter the vessel from the top through the closure. Entrance of air by these methods is poor; moreover, the air has to traverse the length of the neck of the vessel. For these reasons, the conventional flask systems are inferior to the air-sparged fermentor system in achieving high levels of dissolved oxygen in the medium. Despite the need for improved small-scale systems and technology, the same has not been available.

OBJECTS OF THE INVENTION

It is therefore an object of the present invention to provide a novel and improved means, in the field of biotechnology, for the culturing of aerobic microorganisms for increased growth and/or production of metabolites, involving design of fermentation vessel systems affording improved aeration of microorganism cultures.

Another object of this invention is to provide an improved fermentation vessel utilizable for the scale up of fermentation processes to bench top or pilot size fermentors.

These and other objects, features and advantages of the invention will be seen from the following description and the accompanying drawings.

SUMMARY AND DETAILED DESCRIPTION OF THE INVENTION

The invention concerns a container system for the aerobic cultivation of a selected biological entity such as a microorganism or cell line, in a suitable growth medium.

In one preferred embodiment the invention concerns a container apparatus for culturing, for simplicity sometimes referred to hereinafter as a culture bottle for cell growth by artificial cultivation of a selected biological entity in a liquid growth medium. Preferably, the culture bottle is a round flat bottom bottle, being radially symmetrical about a central axis and adapted for rotary shaking and vortexing of liquid to optimize aeration of its liquid content during shaking, the bottle further having aeration enhancing means serving the break up of the surface of the vortexing liquid comprising a symmetrically spaced array of annular baffles, preferably radial, and peripheral baffles located at the inner surface of the base of the bottles.

Preferably, the array of baffles is a quadrilateral array or a trilateral array.

Preferably, the quadrilateral array of baffles has radial spacing expressed in degrees approximately as 90, 180, 270 and 360 degrees for the peripheral baffles and 45, 135, 225 and 315 degrees for the annular baffles.

The trilateral array of baffles preferably has radial spacing expressed in degrees approximately as 120, 240, and 360 degrees for the peripheral baffles and 60, 180, and 360 degrees for the annular baffles.

Each peripheral baffle preferably comprises a baffle member with curvature toward the direction of vortexing, and in one embodiment each peripheral baffle comprises a baffle member with opposite curvature counter to the direction of vortexing.

Preferably, the annular baffles are radially spaced from the peripheral baffles. In one embodiment, the peripheral baffles are bridge baffles connecting the side walls and the base of the bottle such that the base perimeter is open to vortex liquid flow. Also preferred is the embodiment where the peripheral baffles are baffles blocking the base perimeter but spaced from the adjacent side wall such that the annular zone above the base perimeter is open to vortex liquid flow.

In another preferred aspect the culture bottle according to the invention comprises a vortexing chamber, a shoulder, a neck, and splash guard means depending from and within the shoulder and configured in an annular array of V-baffles. Each V-baffle comprises downwardly projecting sides converging in a radially aligned V-apex edge adapted to fragment and centrally and alterally divert the ascent of liquid splashing upwardly from the vortexing chamber toward the neck of the bottle. Preferably, the V-baffles each have the same shape and spacing and are mutually contiguous, and have an inner surface that substantially coincides with an imaginary cylindrical surface that is a downward extension of the inner surface of the neck of the bottle.

The culture bottle according to the invention has an open neck for purposes of enhanced aeration, preferably with a wide mouth opening, and a gas-permeable aeration closure for the open neck comprising filter material. In a preferred embodiment, the aeration closure comprises first and second open-top concentric closures for the open neck, the closures preferably being mutually nestable with the neck. The first closure comprises a radially segmented and apertured raised scaffold centered in its open-top and adapted to support a gas-permeable filter layer material in co-extensive covering relation allowing gas transport into and from the closed bottle. The second closure comprises a radially segmented and apertured raised scaffold centered in its open-top. The open neck and first and second closures are adapted to fit together in sealed closured relation with a filter layer material secured in place in gas filtering relation between the first and second closures.

In a preferred form, the first closure and/or the second closure comprises radial fins adapted to cause circumferential movement of air when a bottle sealed with the aeration closure is under rotary shaking action to thereby promote gas flow through the filter material and facilitate aeration of the bottle interior.

BRIEF DESCRIPTION OF THE DRAWINGS

The invention will be more fully understood by reference to the accompanying drawings in which:

FIGS. 2a to 8a and FIGS. 2b to 8b are views similar to those of FIGS. 1 and 2 of annular baffles and peripheral baffles in a culture vessel, FIGS. 2a to 4a and 2b to 4b showing what may be regarded as conventional baffle arrays and FIGS. 5a to 8a and 5b to 8b showing preferred embodiments of baffle arrays of the invention;

Referring to FIG. 1, the culture bottle or container 10 is round and symmetrical about a center axis 11 and has a neck 12 with a relatively wide mouth 13 defining an opening 14. The bottle has inner and outer walls 10a, 10b, a shoulder 19, a chamber 21 for mixing and vortexing a liquid growth medium under rotation, and a base 22. At the shoulder 17 and as an integral part, a splash guard baffle array 16 is provided. The array 16, best seen in FIG. 1a, is a circumferential array of individual contiguous V-shape baffles 17 of identical shape, each of which has a V-baffle apex 18 formed by opposed downwardly converging side walls 19, and an inner surface 20 that is substantially in effect an extension of the inner wall 10a of the neck 12 thus allowing free flow of air upward and downward from and into the vortexing chamber 21. On the inner surface 10a of the base 22 a symmetrical array of annular baffles 23 and peripheral baffles 24 is located, the array having a center 27 with respect to which liquid in the bottle 10 in a volume indicated by the liquid level line 25 in dotted outline can be vortexed by rotation or shaking. The baffle arrays can have different patterns such as the trilateral array of annular and peripheral baffles of FIG. 6b or the quadrilateral array of FIG. 2. The baffles can have different shapes such as a linear segment on a radius, or an arcuately curved baffle with forward or reverse curvature (FIGS. 1 and 2). One preferred embodiment is a bridge baffle 24c (FIGS. 7a and 7b) where the baffle is disposed at the circumferential edge 22a of the base but spanning and leaving the edge open, with attachment on the base and the inner wall 10a of the chamber. The opening 24e below the bridge baffle allows the partial flow of vortexing liquid in the bottle and is configured to cause cavitation and aeration during vortexing of a liquid. Another preferred embodiment is an L-shaped baffle or L-baffle 24d shown in FIGS. 8a and 8b. The L-baffle 24d is attached at the edge 22a of the base and has an upstanding fin 24 extending above the liquid level line 25 and spaced from the inner wall surface 10a.

Figure 1:
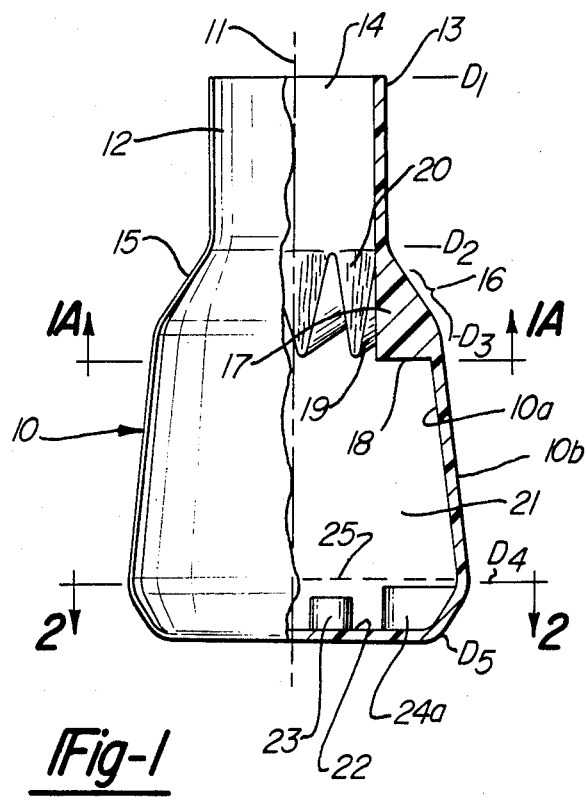
FIG. 1 is a view in side elevation partly in section of a preferred embodiment of a culture bottle according to the invention.
Figure 1A:
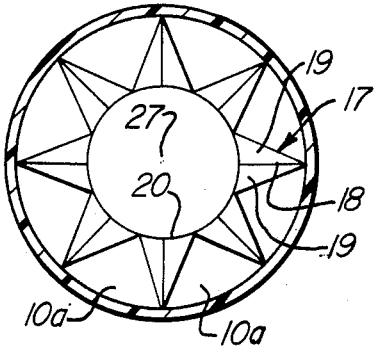
FIG. 1a is a view of the culture bottle taken on line 1a—1a of FIG. 1.

For sealing or closing the culture bottle so that the culture can be vortexed aseptically and aerated without sparging, closure elements are provided comprising an outer aeration closure or cap 30, an inner aeration closure or cap seat 40 and a filter cup 50 (FIGS. 9 to 12). In a preferred embodiment, the cap, filter cup, cap seat and bottle mouth 13 fit together and are mutually nestable. The cap 30 includes a cylindrical base 31 with a co-axial central opening 32. The base has a shoulder 33, a scaffold 34 with a closed top 35, a sidewall 36 having circumferentially spaced vertical fins 37 with openings or fenestration 38 therebetween. The cap seat 40 includes a base 41 with a co-axial central opening 41a, a first shoulder 42, a cap support 43, a second shoulder 43a with lateral fenestration 48a, a scaffold 44 with a closed top 45, a sidewall 46 having circumferentially spaced vertical fins 47 with sidewall fenestration therebetween. The filter cup 50 which may be made of a suitable air-permeable filter material such as layered gauze is shaped to have a sidewall 51 and an opening 52 so that it can be placed in co-extensive covering relation over the lateral fenestration 48a and sidewall fenestration 48b of the cap seat 40.

In a typical culture growth operation, the apparatus (bottle, cap, cap seat, and filter) is preliminarily sterilized, the liquid growth medium is introduced to the bottle in a volume sufficient to fill the same to the liquid level line 25, and the medium is seeded with a selected seed culture or microorganism culture. The bottle is then closured stepwise by nesting or placing the cap support 40 over the mouth 13 of the bottle, nesting the fenestrated scaffold 44 within the filter cup 50, and capping over the filter cup 50 with the outer cap 30. For closing the bottle, the cap support and its opening 41a and the mouth 13 are shaped so that the parts nest or fit together closely as by a telescoping relation or a snap fit or lock fit or other suitable removably secure fit. Similarly, the cap and its cap opening 32 and the filter cup support 43 and shoulder 43a are shaped so the parts nest or fit together closely. The latter fit is such that the filter cup 50 can be placed over the cup support scaffold to cover its fenestrations and thus placed over the cup support is held in place sandwiched between the cap and cap support by the nesting placement of the cap 30 and cap shoulder 33 on the cup support shoulders 42 and 43a. Thus air flow or gas flow through the fenestrations 38, 48a and 48 must pass through the sterile filter 50. The sealed culture bottle is then incubated under cell growth conditions for a predetermined period with steady rotation and vortexing to achieve vortexing of the seeded liquid. During vortexing, the liquid flow is both annular and circumferential in the direction of vortexing. The liquid flow is broken up by the mentioned array of baffles so that advantageously aeration of the liquid is enhanced or optimized with consequent improvement in the growth rate of the desired microbiological entity or seed culture. A certain amount of splashing occurs due to the baffling action and even in the absence of baffling, which splashing in turn is directly proportional to the speed of rotation. To overcome the splashing so that the filter cup 50 will remain dry, the splash guard 16 serves to block and laterally divert any splashing that may be moving directly upward from the baffled vortexing chamber.

EVALUATION FOR AERATION CAPACITY AND CONTROL OF SPLASHING

Preferred embodiments of the bottle or flask containers of the invention were evaluated for aeration capacities following the sulfite oxidation method of Cooper et al., 1944 (Ind. Eng. Chem. 36:504). Thus the flasks were filled with 50 ml of sulfite solution and covered with one layer of gauze. The control flasks consisted of: a. unbaffled 250-ml Erlenmeyer flask, b. 300-ml commercial (Bellco) shallow baffled, and c. 300-ml commercial (Bellco) deep baffled.

Also the above flasks were evaluated for wetting of gauze during a fermentation run. For this comparison, 50 ml of the following medium was dispensed to the flasks: 4% sucrose, 4% cotton seed meal. The flasks were inoculated with 10% inoculum of *Streptomyces chartreusis* and incubated for 1–2 days with shaking, 180 rpm (Model G-53 New Brunswick shaker). Results in Table 1 show different aeration capacities in the different flask designs. Of particular interest is Flask #18 with an oxygen absorption rate (OAR) value of 5.1 mM oxygen/liter/min. The baffle system of this flask is characterized by 4 pairs of baffles ("butterfly" design) on the bottom side of the flask and complemented with an open cross baffle on the bottom center of the flask. This baffle system proved to be very effective in mixing the medium in the flask.

TABLE 1

Evaluation of oxygen absorption rate (OAR, mM oxygen/liter/min.) and wetting of closure of flasks with different baffle system while shaken (C = clean; SC = slightly clean; MD = medium dirty; D = dirty).

| Flask by Figure No. | 180 RPM OAR | closure condition | 200 RPM OAR | closure condition |
|---|---|---|---|---|
| 1, 2 | 5.10 | MD | 5.90 | MD |
| 2a, 2b | 1.90 | D | 1.74 | MD |
| 3a, 3b | 1.50 | MD | 1.39 | D |
| 4a, 4b | 1.60 | D | 1.78 | D |
| 5a, 5b | 2.81 | MD | — | — |
| 6a, 6b | 3.69 | MD | 4.90 | MD |
| 7a, 7b | 3.30 | MD | 4.50 | MD |
| 8a, 8b | 3.18 | MD | 3.90 | MD |
| Control A | 0.85 | C | 0.90 | C |
| B | 1.13 | C | 1.28 | C |
| C | 2.33 | SC | 2.77 | SC |

Control A = 250-ml Erlenmeyer unbaffled flask; B = 300-ml (Bellco) shallow baffled flask; C = 300-ml (Bellco) deep baffled flask.

The OAR values and degree of cap wetting is shown in Table 1.

EXAMPLE 3: CLOSURE DESIGN

The closure of FIGS. 9 to 12 is a slip-on type closure which fits snugly over the lip of the flask. The sidewall of the closure is lined with a gauze and the outer shell is provided with ribs or fins. The ribs are designed to trap air, and by the gyratory action of the flask during shaking, enables active diffusion of the trapped air towards the inside of the flask.

EXAMPLE 4: AERATION CAPACITIES OF THE FLASK SYSTEM

The flask embodiment of the invention (FIGS. 1 and 2) and its closure (FIGS. 9 to 12) both in unbaffled and baffled form were evaluated for aeration capacities in comparison with commercially available flasks: 250-ml Nalgene polypropylene flask tested with a cotton closure; 300-ml Bellco shallow and deep baffled flasks, tested with commercial (Kaputs) plastic closure.

The aeration capacities of the flasks were evaluated using the sulfite oxidation procedure of Cooper et al., supra. Thus, 50-ml quantities of sulfite solution were dispensed into the flasks and shaken in a Model G-53 New Brunswick shaker at various RPM level. The aeration values are expressed as oxygen absorption rates (OAR) in mM oxygen/liter/min. The experimental results shown in Table 2 clearly indicate the superiority of the baffled and unbaffled (i.e., without base-mounted baffling) over the currently available flasks.

TABLE 2

Oxygen absorption rate (OAR), 50 ml sulfite/flask, Model G-53 New Brunswick shaker, 26° C.)

| Flask type and closure | 100 rpm | 150 rpm | 200 rpm | 250 rpm |
|---|---|---|---|---|
| 250-ml Nalgene, unbaffled (cotton closure) | 0.38 | 0.65 | 0.86 | 0.98 |
| 300-ml FIGS. 1, 2, 9–12 unbaffled | 0.48 | 0.78 | 1.03 | 1.51 |
| 300-ml Bellco, shallow baffle (Kaputs closure) | 0.44 | 0.85 | 1.05 | 1.72 |
| 300-ml Bellco, deep baffle | 0.59 | 1.40 | 2.16 | 3.66 |

TABLE 2-continued

| | Oxygen absorption rate (OAR), 50 ml sulfite/flask, Model G-53 New Brunswick shaker, 26° C.) | | | |
|---|---|---|---|---|
| Flask type and closure | 100 rpm | 150 rpm | 200 rpm | 250 rpm |
| (Kaputs closure) | | | | |
| 300-ml FIGS. 1, 2, 9-12 baffled | 0.69 | 1.65 | 4.04 | 6.59 |

CULTIVATION OF MICROORGANISMS

Figure 2:
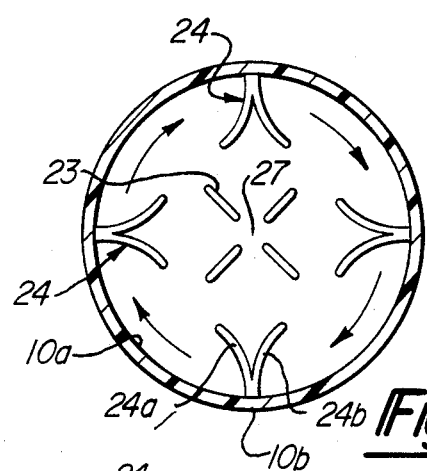
Figure 2A:
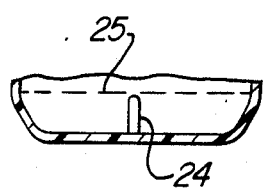
Figure 2B:
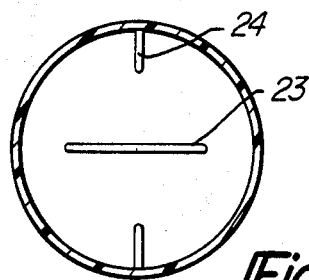
Figure 3A:
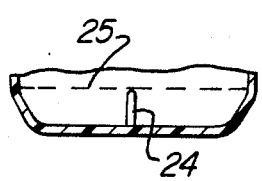
Figure 3B:
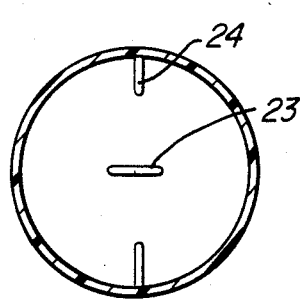
Figure 4A:
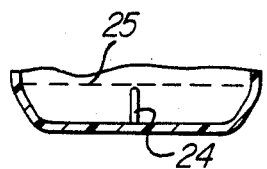
Figure 4B:
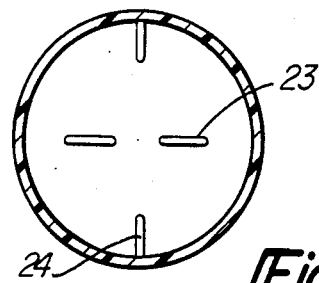
Figure 5A:
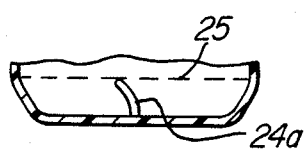
Figure 5B:
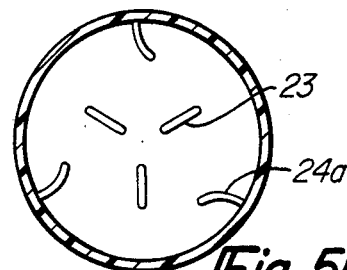
Figure 6A:
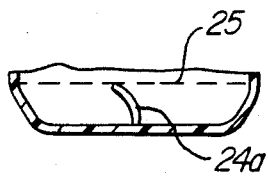
Figure 6B:
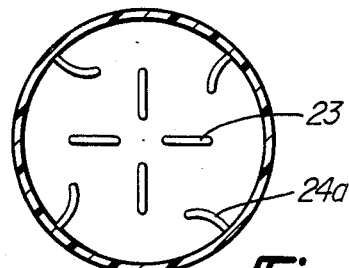
Figure 7A:
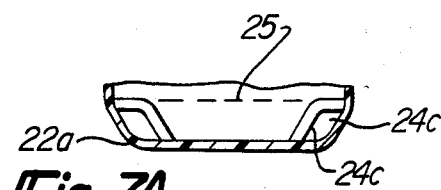
Figure 7B:
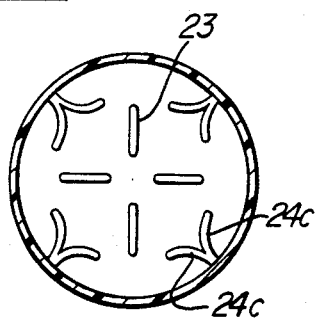
Figure 8A:
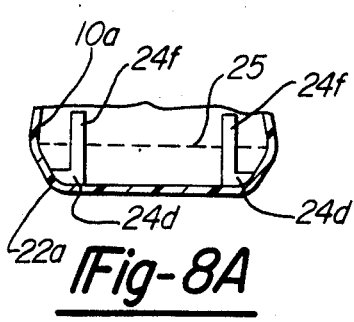
Figure 8B:
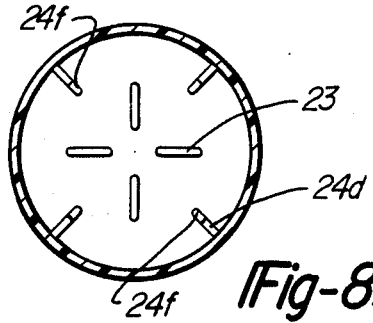
Figure 9:
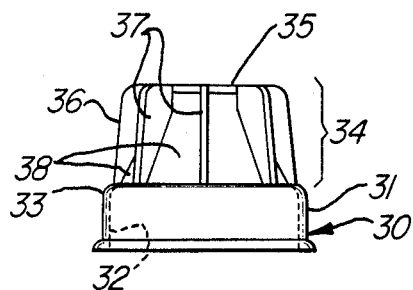
FIGS. 9 and 10 are side and top views respectively of an outer aeration closure according to the invention.
Figure 10:
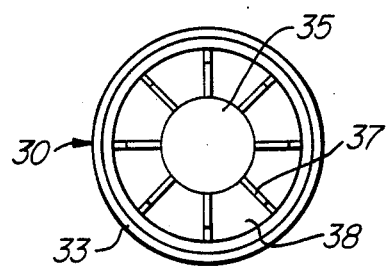
Figure 11:
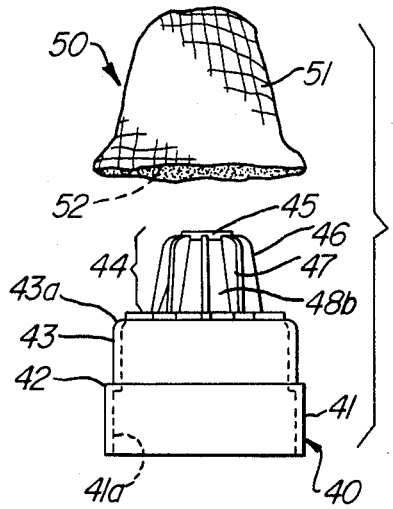
FIGS. 11 and 12 are side and top views respectively of an inner aeration closure that, according to the invention, is nestable with the open neck of a culture bottle and the outer closure.
Figure 12:
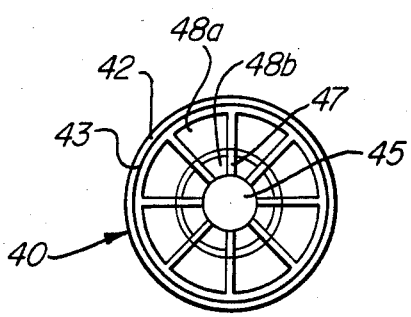

Microorganisms representative of a single-celled prokaryote (*Escherichia coli*), a single-celled eukaryote (*Saccharomyces cerevisiae*), an actinomycete (*Streptomyces chartreusis*), and a fungus (*Penicillium avellaneum*) were evaluated for growth in the flask system of FIGS. 1 and 2. For comparison, the following conventional flasks were evaluated: 250-ml Nalgene unbaffled polypropylene flask (cotton closure), and 300-ml Bellco shallow and deep baffled flasks (Kaputs closure).

A. *Escherichia coli*

The seed was prepared by inoculating a loopful of the organism into 50 ml of Nutrient Broth medium (Difco) contained in a 250-ml Erlenmeyer flask. The inoculated flask was incubated in a static condition overnight at 37° C. The microbial growth in the flask was used as seen inoculum.

One ml of seed was used to inoculate 50 ml of growth medium contained in the various flasks under study. The growth medium consisted of the following composition: 3.0% glucose, 1.575% $K_2HPO_4$, 0.675% $KH_2PO_4$, 0.1% yeast extract (Difco), 0.45% $(NH_4)_2SO_4$, 0.06% sodium citrate, and 0.015% $MgSO_4.7H_2O$. One drop of P-2000 polyglycol antifoam was added to each flask, then incubated at 37° C. for 18 hours at 200 RPM (Model G-53 New Brunswick shaker).

The results in Table 3 shows that the present baffled flask gave the highest *E. coli* growth, a growth value of 7.09 (optical density at 555 nm).

TABLE 3

Comparison of flasks of the invention with conventional flasks for the cultivation of single-celled prokaryote, *Escherichia coli* (50 ml medium/flask, shaken for 18 hours at 37° C., 200 RPM Model G-53 New Brunswick shaker).

| Flask type and closure | Growth (O.D., 555 nm) | Standard deviation |
|---|---|---|
| 300-ml, FIGS. 1, 2, 9-12 baffled (FIG. 9-12 closure) | 7.09 | 0.14 |
| 300-ml, Bellco, deep baffle (Kaputs plastic closure) | 5.99 | 0.20 |
| 300-ml, FIGS. 1, 2, 9-12, unbaffled (FIG. 9-12 closure) | 5.36 | 0.08 |
| 300-ml, Bellco, shallow baffle (Kaputs closure) | 4.68 | 0.23 |
| 250-ml, Nalgene, unbaffled, (cotton closure) | 3.96 | 0.09 |

"Average of 9 samples. Tukey's W-procedure for statistical comparison of means for differences ($W_{0.05}$ = 0.21) shows that the growth values are all significantly different.

B. *Saccharomyces cerevisiae:*

The seed was prepared by transferring a loopful of the organism from an agar slant into 50 ml Sabouraud Dextrose broth (Difco). The inoculated flask was incubated in a static condition overnight at 34° C. The microbial growth in the flask was used as seed inoculum.

One ml of seed was used to inoculate 50 ml of growth medium contained in the various flasks under study. The growth medium consisted of the following composition: 5.0% glucose, 1.0% $(NH_4)_2SO_4$, 0.6% $KH_2PO_4$, 0.1% yeast extract (Difco), 0.3% $MgSO_4.7H_2O$, 0.01% $CaCl_2.2H_2O$, and 0.01% NaCl. One drop of P-2000 polyglycol antifoam was added to each flask, then incubated at 34° C. for 18 hours at 200 RPM (Model G-53 New Brunswick shaker).

Results in Table 4 show that the best microbial growths were obtained in the baffled and unbaffled flasks of the invention, 5.63 and 5.57, respectively.

TABLE 4

Comparison of flasks of the invention with conventional flasks for the cultivation of a single-celled eukaryote, *Saccharomyces cerevisiae* (50 ml medium/flask, shaken for 18 hours at 200 RPM, 34° C.)

| Flask type and closure | Growth (O.D. at 555 nm) | Standard deviation |
|---|---|---|
| 300-ml FIGS. 1, 2, 9-12 baffled | 5.63 | 0.19 |
| 300-ml FIGS. 1, 2, 9-12 unbaffled | 5.57 | 0.16 |
| 300-ml Bellco, shallow baffle (Kaputs closure) | 5.32 | 0.19 |
| 300-ml Bellco, deep baffle (Kaputs closure) | 5.31 | 0.18 |
| 250-ml Nalgene, unbaffled (cotton closure) | 5.19 | 0.15 |

"Average of 9 samples. Tukey's W-procedure for statistical comparison of means for differences is shown below, $W_{0.05}$ = 0.24 (numbers underscored by the same line indicates no significant differences):
5.19 5.31 5.32    5.57 5.63

C. *Streptomyces chartreusis:*

The seed was prepared by transferring microbial growth of Streptomyces chartreusis from an agar slant into 50 ml of fermentation medium contained in a 300-ml Bellco shallow baffled flask. The fermentation medium consisted of the following ingredients: 0.5% yeast extract (Amber Labs), 0.1% glucose, 2.5% dextrin (American Maize), 0.5% casein digests (Sheffield), 0.3% spray dried meat solubles (Jen-Kim), and 0.2% $CaCO_3$. The inoculated flask was incubated by shaking, 180 RPM, at 33° C. After 2 days, good microbial growth was obtained which was straw colored in appearance; this was used as seed inoculum.

Two ml of the seed was used to inoculate the various flask under study. The flasks contained 50 ml of the above fermentation medium. One drop of P-2000 polyglycol antifoam was added to each flask after inoculation and the flasks were incubated by shaking at 200 RPM (Model G-53 New Brunswick shaker) for 24 hours, 26° C.

Results in Table 5 show that the best growth is obtained in unbaffled flask (FIGS. 1, 2 and 9-12), 27.73% sedimentation. In another case, the baffled flask of (FIGS. 1, 2 and 9-12) produced excellent growth, but more importantly, the organism in that flask produced the most intense pigmentation as evidenced by brownish black discoloration in the fermentation sample.

TABLE 5

Comparison of flasks of the invention with conventional flasks for the cultivation of an actinomycete, *Streptomyces chartreusis* (50 ml medium/flask, shaken for 24 hours at 200 RPM, 26° C.)

| Flask type and Closure | Growth appearance of fermentation | % Growth (sediment) | Standard deviation |
|---|---|---|---|
| 300-ml FIGS. 1, 2, 9–12 baffled | Brownish black | 19.20 | 0.70 |
| 300-ml Bellco, deep baffle (Kaputs Closure) | Dark Brown | 19.70 | 0.79 |
| 300-ml Bellco, shallow baffle (Kaputs Closure) | Light Brown | 14.43 | 1.16 |
| 250-ml Nalgene, unbaffled (cotton Closure) | Straw color | 17.37 | 1.15 |
| 300-ml FIGS. 1, 2, 9–12 unbaffled | Straw color | 27.73 | 1.96 |

<sup>a</sup>Average of 3 flasks. Tukey's W-procedure for statistical comparison of means for differences is shown below. $W_{0.05} = 3.83$ (numbers underscored by the same line no significant differences):
14.43  17.37  19.20  19.70   27.73

D. *Penicillium avellaneum*:

The seed was prepared by transferring mycelial fragments of the organism from an agar slant into 50 ml of Sabouraud Dextrose broth (Difco) medium contained in a 300-ml Bellco shallow baffled flask. The inoculated flask was incubated by shaking at 180 RPM, 33 C for 2 days. The microbial growth from this flask is used as seed inoculum.

Two ml of the seed was used to inoculate the various flask under study. The flasks contained 50 ml of fermentation medium, particularly Potato Dextrose borth (Difco). One drop of P-2000 polyglycol antifoam was added to each flask after inoculation then the flasks were incubated by shaking at 200 RPM (Model 6-53 New Brunswick shaker) for 3 days, 26° C.

Results in Table 6 show different types of growth in the various flasks. Notably, the unbaffled flask of the invention produced the best growth, 30.5% sedimentation; the corresponding baffled flask, on the other hand, produced growth of a different morphology, particularly a mycelial mat instead of pellets.

TABLE 6

Comparison of flasks of the invention with conventional flasks for the cultivation of a fungus, *Penicillium avellaneum* (50 ml medium/flask, shaken for 3 days at 200 RPM, 26° C.).

| Flask type and Closure | Growth morphology | % Growth (sediment) | Standard deviation |
|---|---|---|---|
| 300-ml, FIGS. 1, 2, 9–12 unbaffled | Very fine pellets with occasional mycelial strands | 30.5 | 1.70 |
| 250-ml Nalgene, unbaffled (cotton closure) | Fine Pellets | 25.1 | 1.07 |
| 300-ml Bellco, shallow baffle (Kaputs closure) | Fine pellets | 21.0 | 1.99 |
| 300-ml Bellco, deep baffle (Kaputs closure) | Large irregular pellets; mycelial film on flask sides | 9.5 | 0.75 |
| 300-ml, FIGS. 1, 2, 9–12 baffled | Mycelial mat on flask sides; no pellets | 3.3 | 0.15 |

<sup>a</sup>Average of 3 flasks. Only pourable fermentation samples were evaluated. Mycelial mat build-up on the sides of the flasks, particularly the baffled flask of the invention and deep baffled Bellco accounts for the low sedimentation values for these flasks.

The container and closure apparatus of the invention can be made of any suitable materials which may be conventional materials used in container, filter, glassware, or plasticware technology. A preferred container embodiment is a unitary polypropylene or similar plastic, flask, either baffled or unbaffled preferably base-baffled as illustrated in FIG. 1, with closure elements as in FIGS. 9 to 12, preferably made by injection molding, suitable for sterilization and reuse or being disposable. The shape and size of the apparatus is not particularly critical. 2-liter and 300-ml. sizes are preferred. For example, a preferred size embodiment for a 300-ml. of medium, shown in FIG. 1, has diameters and spacing in inches, as follows:

| | |
|---|---|
| $D_1$ 1.75 | $D_1$–$D_2$ 1.75 |
| $D_2$ 1.75 | $D_2$–$D_3$ 1.0 (slant height) |
| $D_3$ 2.75 | $D_3$–$D_4$ 2.5 (slant height) |
| $D_4$ 3.25 | $D_4$–$D_5$ 0.5 (slant height) |
| $D_5$ 2.5 | Base baffle height, Ca 0.5 |

While the invention is described in detail in the foregoing specification, it will be realized by those skilled in the art that considerable variation can be made in such detail without departing from the spirit and scope of the claims which follow:

I claim:

1. A culture bottle for cell growth by artificial cultivation of a selected biological entity in a growth liquid, the bottle being radially symmetrical about a central axis and adapted for rotary shaking and vortexing of liquid to optimize aeration of liquid content during shaking, the bottle further having aeration enhancing means serving to break up the surface of the vortexing liquid comprising a symmetrically spaced array of annular baffles and peripheral baffles located at the inner surface of the base of the bottle.

2. A culture bottle according to claim 1 where the annular baffles are radial baffles.

3. A culture bottle according to claim 1 here the array of baffles has radial spacing expressed in degrees approximately 90, 180, 270 and 360 degrees for the peripheral baffles and 45, 135, 225 and 315 degrees for the annular baffles.

4. A culture bottle according to claim 1 where the array of baffles is a quadrilateral array.

5. A culture bottle according to claim 4 where each peripheral baffle comprises a baffle member with curvature toward the direction of vortexing.

6. A culture bottle according to claim 5 where each peripheral baffle comprises a baffle member with opposite curvature counter to the direction of vortexing.

7. A culture bottle according to claim 1 where the array of baffles is trilateral array.

8. A culture bottle according to claim 1 where the array of baffles has radial spacing expressed in degrees approximately as 120, 240, and 360 degrees for the peripheral baffles and 60, 180, and 300 degrees for the annular baffles.

9. A culture bottle according to claim 7 where each peripheral baffle comprises a baffle member with curvature toward the direction of vortexing.

10. A culture bottle according to claim 1 where the annular baffles are radially spaced from the peripheral baffles.

11. A culture bottle according to claim 1 where the peripheral baffles comprise bridge baffles connecting the side walls and the base of the bottle such that the base perimeter is open to vortex liquid flow.

12. A culture bottle according to claim 1 where the peripheral baffles comprises baffles blocking the base perimeter but spaced from the adjacent side wall such that the annular zone above the base perimeter is open to vortex liquid flow.

13. A culture bottle according to claim 1 having a vortexing chamber, a shoulder, a neck, and splash guard means depending from and within the shoulder and configured in an annular array of V-baffles each having downwardly projecting sides converging in a radially aligned V-apex edge adapted to fragment and centrally and laterally divert the ascent of liquid splashing upwardly from the vortexing chamber toward the neck of the bottle.

14. A culture bottle according to claim 13 where the V-baffles have the same shape and spacing and are mutually contiguous.

15. A culture bottle according to claim 14 where each V-baffle has an inner surface that substantially coincides with an imaginary cylindrical surface that is a downward extension of the inner surface of the neck of the bottle.

16. A culture bottle according to claim 1 having an open neck and a gas-permeable aeration closure for the open neck comprising filter material.

17. A culture bottle according to claim 16 where the aeration closure comprises first and second open-top concentric closures for the open neck, the first closure comprising a radially segmented and apertured raised scaffold centered in its open-top adapted to support a gas-permeable filter layer material in co-extensive covering relation allowing gas transport into and from the closure bottle, the second closure comprising a radially segmented and apertured raised scaffold centered in its open-top, the open neck and first and second closures being adapted to fit together in sealed closured relation with a filter layer material secured in place in gas filtering relation between the first and second closures.

18. A culture bottle according to claim 17 where the second closure comprises radial fins adapted to cause circumferential movement of air when a bottle sealed with the aeration closure is under rotary shaking action to thereby promote gas flow through the filter material and facilitate aeration of the bottle interior.

19. A culture bottle according to claim 17 where the open neck, and the first and second closures are mutually nestable.

20. A culture bottle according to claim 17 where the first closure comprises radial fins adapted to cause circumferential movement of air when a bottle sealed with the aeration closures is under rotary shaking action to thereby promote gas flow through the filter material and facilitate aeration of the bottle interior.

21. A culture bottle having a vortexing chamber, a shoulder, a neck, and splash guard means depending from and within the shoulder and configured in an annular array of V-baffles each having downwardly projecting sides converging in a radially aligned V-apex edge adapted to fragment and centrally and laterally divert the ascent of liquid splashing upwardly from the vortexing chamber toward the neck of the bottle.

* * * * *